United States Patent [19]

McNeil et al.

[11] Patent Number: 5,229,610

[45] Date of Patent: Jul. 20, 1993

[54] METHOD AND APPARATUS FOR DETECTING HYDROGEN-CONTAINING COMPOUNDS

[75] Inventors: James A. McNeil, Boulder, Colo.; David S. Oakley, Lake Oswego, Oreg.; Charles E. Price, Boulder, Colo.

[73] Assignee: Colorado School of Mines, Golden, Colo.

[21] Appl. No.: 833,434

[22] Filed: Feb. 6, 1992

Related U.S. Application Data

[63] Continuation-in-part of Ser. No. 651,304, Feb. 6, 1991.

[51] Int. Cl.$^5$ ............................................. G01N 23/00
[52] U.S. Cl. ...................................... 250/308; 250/307
[58] Field of Search ................... 250/308, 307, 432 R, 250/253, 370.02

[56] References Cited

U.S. PATENT DOCUMENTS

| | | | |
|---|---|---|---|
| 3,043,955 | 7/1962 | Friedland et al. | 250/83.3 |
| 3,695,848 | 10/1972 | Taguchi | 23/254 E |
| 4,186,303 | 1/1980 | Smith et al. | 250/253 |
| 4,194,115 | 3/1980 | Whitehead et al. | 250/308 |
| 4,417,142 | 11/1983 | Malmqvist et al. | 250/253 |
| 4,871,914 | 10/1989 | Simon et al. | 250/370.02 |
| 4,960,998 | 10/1990 | Peter | 250/432 R |

FOREIGN PATENT DOCUMENTS 051025 6/1972 Japan ................................... 256/250

OTHER PUBLICATIONS

Evans, R. "The Atomic Nucleus", McGraw-Hill Book Co. (1955) pp. 799 and 818.

Primary Examiner—Paul M. Dzierzynski
Assistant Examiner—Richard Hanig
Attorney, Agent, or Firm—Sheridan, Ross & McIntosh

[57] ABSTRACT

A low-cost detector of hydrogen-containing compounds in gas or thin-film samples is disclosed. The device preferably includes an alpha particle source, an energy degrading medium, a charged particle detector (e.g. a solid state diode detector), and amplification, threshold, counting, logic, timing circuits, humidity correction apparatus, and alarm/display. The invention relies upon the use of the energy degrading foil to pass selectively certain particles. Energetic alpha particles from a radioactive source enter the sample and hydrogen nuclei, or protons, elastically scattered by alpha particles, are able to penetrate the energy degrading foil which is thick enough to stop the alpha particles. The protons are detected and a suitable output signal can be produced to provide an accurate measure of the quantity of hydrogen in the gas or thin-film sample. The hydrogen detector can be combined with a smoke detector to produce an apparatus capable of detecting both smoke and hydrogen. This technology can also be used to reduce noise and block light penetration in a radon detection application.

26 Claims, 3 Drawing Sheets

METHOD AND APPARATUS FOR DETECTING HYDROGEN-CONTAINING COMPOUNDS

RELATED APPLICATION

This application is a continuation-in-part of co-pending U.S. patent application Ser. No. 07/651,304 filed on Feb. 6, 1991 which is incorporated herein by reference in its entirety.

FIELD OF THE INVENTION

This invention generally relates to the use of particle detection for identifying the presence of certain substances and in particular to the low cost detection of hydrogen atoms in gas or thin film samples, including potentially hazardous gases containing hydrogen, such as natural gas and propane, as well as nonhazardous hydrogen-containing gases, such as water vapor, through the use of a degrading foil. In another embodiment, the degrading foil can also be used to block noise and light penetration in a low cost device for detecting radon and radon daughters.

BACKGROUND OF THE INVENTION

Each year people are injured or killed as a result of the chemical toxicity or explosive flammability of many hydrogen-containing gases such as natural gas and propane. Such hydrogen-containing gases are commonly used or found in a residence or workplace. A number of methods exist to detect hydrogen-containing gases but many of the methods suffer drawbacks when employed in residential and industrial applications.

U.S. Pat. No. 3,695,848 by Taguchi discloses an apparatus for detecting hydrogen-containing reducing gases, by heating an n- or p-type metal oxide semiconductor such as tin oxide to 150° C. to 250° C. Reducing gases such as $H_2$, $CO$, $C_2H_2$, $CH_4$, $C_2H_5OH$, $C_3H_8$ and $C_4H_{10}$ lowers the resistance of the semiconductor through combustion heating. The decreased resistance permits more current to flow across the semiconductor which triggers an alarm at desired concentrations.

The device has a number of disadvantages. First, the device measures only those hydrogen-containing gases which are reducing. Toxic hydrogen-containing gases such as ammonia and sulfuric acid are not detected by the device. Second, the device requires a high power input to maintain the desired temperature of the ceramic insulator. As a result, it is not practical to power the device for long periods using a battery. Third, the device is incapable of detecting hydrogen-containing compounds in an oxygen depleted environment that will not support a combustion reaction or above the upper explosive limit of such compounds, which is a concentration of about 15% by volume for methane. Fourth, the device creates a risk of explosion for explosive hydrogen-containing gases such as natural gas and propane due to the high temperature of the semiconductor. Finally, the accuracy of the device may be decreased by the accumulation of residue on the semiconductor. In particular, grease generated in a kitchen environment may produce a carbon residue, short circuiting the sensor.

U.S. Pat. No. 4,194,115, by Whitehead, et al., discloses a device employing two charged particle detectors to determine the ratio of helium to hydrogen in a sample gas. The detectors measure the energy loss of the products of collisions between alpha particles on the one hand and either hydrogen or helium on the other. The detectors are aligned such that the high energy recoil protons from the collisions between alpha particles and hydrogen nuclei, but not helium particles, pass through the first detector and impact the second detector.

This device also suffers from a number of disadvantages. First, accuracy of the device's measurement is decreased by the device's use of baffles to limit the particle spectrum impacting the detectors to a specific predetermined forward scattering angle. Second, the device's use of coincidence counts between the two detectors to detect the ratio of helium to hydrogen is inherently inefficient as a result of the need for coincidence detection of two events. Third, since the barrier (e.g., the first detector) used to stop alpha or helium particles must be a semiconductor, the available thicknesses of the barrier are restricted. This may complicate the optimization of the barrier thickness to permit a maximum number of recoil protons and a minimum number of alpha or helium particles to pass through the barrier. In short, the barrier will either be too thin and permit additional alpha or helium particles to contact the second detector or too thick and fail to permit substantially all recoil protons to contact the second detector. Fourth, the device is designed for use in outer space and will not operate in air (oxygen and nitrogen). The heavier oxygen/nitrogen nuclei will scatter a large fraction of the primary alpha particles into the first detector creating inaccurate measurements. Finally, the device's use of separate detectors requires additional supporting circuitry which substantially increases the complexity and cost of the device.

There is also a need for a low cost detection device to detect radon and radon daughters in residential and industrial applications. In recent years, the detrimental effects of radioactive materials released into the atmosphere either from radioactive deposits underlying buildings or from materials used in the workplace have become an increasingly serious problem. Numerous people each year contract cancer as a result of such radioactive emissions.

U.S. Pat. No. 4,186,303, by Smith, et al., discloses an apparatus for detecting alpha particles from radon 222 and not radon 220 by enclosing the detector with a semi-permeable membrane which passes alpha particles from radon 222 but not from radon 220. The detector is designed to be placed in a hole in the earth to detect underground deposits of uranium and/or thorium. The apparatus has a number of disadvantages. First, it is designed only for use in detecting underground deposits of uranium and thorium and is not suitable for use in residential and industrial applications for the detection of radioactive materials released into the ambient atmosphere. Second, the apparatus detects only alpha particles from radon 222 and not other radioactive sources such as radon 220, which is a commonly encountered radioactive material in residential and industrial settings. Finally, the apparatus employs two dosimeters which, along with their supporting circuitry, substantially increase the complexity and cost of the device.

U.S. Pat. No. 4,811,714, by Simon et al., discloses an apparatus for continuous determination of gas-carried alpha activity caused by radioactive charge of thorium, uranium, platinum, and their decay products. The device employs a semiconductor sensor and claims improved response by the use of dummy circuitry and the electroplating of radon daughters onto the detector surface. The apparatus has a number of disadvantages. First, the dummy circuitry increases the complexity and cost of the device. Second, the counts arising from radon daughters plated onto the surface of the detector gives rise to inaccuracies in the radon count since the radon daughter concentration is not known a priori and can vary significantly. Finally, there are important limitations on the accuracy of the electrostatic precipitation method due to neutralization processes.

U.S. Pat. No. 4,960,998, by Peter, discloses an apparatus for determination of gas-carried alpha activity caused by the decay of thorium, uranium, plutonium and their decay products. The gas-carried alpha activity from the decay chains of radon 220 and radon 222 is subtracted from a total gas-carried alpha activity measured by the apparatus. The apparatus employs three alpha counters, one to measure total alpha activity, one to measure gas-carried alpha activity of Rn-220 and one to measure the gas-carried alpha activity of Rn-222. The apparatus also has a number of disadvantages. First, the apparatus is not intended to determine the full spectrum of alpha particles generated by radioactive sources, but subtracts out the alpha activity from the decay chains of radon 220 and radon 222. Second, the use of three separate detectors and their supporting circuitry substantially increases the complexity and cost of the device. Accordingly, the device is not suitable for residential and industrial applications which require an inexpensive apparatus to detect the full spectrum of alpha activity generated from radioactive sources.

SUMMARY OF THE INVENTION

The present invention provides a simple and inexpensive device for continuously measuring in gas or thin film samples the concentrations of hydrogen atoms or radon and radon daughters in residential and commercial applications.

In one embodiment, a radioactive source of alpha particles is positioned to cause alpha particles to contact a sample medium. The apparatus includes an energy degrading film of predetermined thickness sufficient to stop substantially all of the alpha particles produced by the radioactive source and permit passage of substantially all of the recoil protons produced when the alpha particles contact hydrogen nuclei in the sample medium. A particle detecting apparatus is positioned on the side of the energy degrading film opposite the radioactive source and (in the preferred embodiment) includes a depletion layer located a predetermined distance from the energy degrading film sufficient for the recoil protons passing through the energy degrading film to deposit energy in the depletion layer. The degrading film is typically a degrading foil such as a metal foil.

The particle detecting apparatus transmits a signal proportional to the energy of the recoil protons deposited in the depletion layer to an amplifying apparatus which amplifies the signal produced by the particle detecting apparatus and preferably sends the amplified signal to a threshold discriminating mechanism which eliminates substantially all signals received from the amplifying apparatus below a specified magnitude.

A logic and timing circuit is preferably connected to the output of the threshold discriminating mechanism to count pulses received from the threshold discriminating mechanism in a specified period of time and a humidity detector is preferably connected to the logic and timing circuit to adjust the output signal of the logic and timing circuit relative to the concentration of $H_2O$ in the sample medium.

In another embodiment, a device uses a single alpha particle source to measure the concentrations of smoke and hydrogen-containing compounds. Recoil protons produced when the alpha particles contact hydrogen nuclei in the sample medium pass through an energy degrading film of a predetermined thickness sufficient to stop substantially all of the alpha particles produced by the radioactive source and permit passage of substantially all of the recoil protons. The recoil protons then contact a particle detector positioned on the side of the energy degrading film opposite the radioactive source. The recoil protons passing through the energy degrading film deposit energy in a depletion layer in the particle detector located a predetermined distance from the energy degrading film. The detecting apparatus produces a signal proportional to the energy of the recoil protons deposited in the depletion layer and transmits the signal to amplifying and comparing circuitry. Additionally, the device includes an ionization level detector for detecting smoke more rapidly than the hydrogen detection method above. The ionization level detector includes a detection chamber for receiving ambient air. Alpha particles from the alpha particle source ionize the air and generate a current in the detection chamber between at least two electrodes, one of which may be the degrading foil.

In another embodiment, a low-noise detector of radon and radon daughters in a sample medium includes a particle detector having a depletion layer and an energy degrading film placed between the sample medium and the particle detector. The degrading film is of a predetermined thickness sufficient to block substantially all light penetration and pass substantially all of the alpha particles from the decay of radon and radon daughters. The depletion layer in the particle detector, which may be a degrading foil such as a metal foil, is located a predetermined distance from the energy degrading film sufficient to permit substantially all of the alpha particles passing through the energy degrading film to deposit energy in the depletion layer. The particle detector produces a signal proportional to the energy deposited in the depletion layer and transmits the signal to an amplifier connected to the particle detector which amplifies the signal. The amplified signal is transmitted to a threshold discriminating mechanism which eliminates signals received from the amplifier below a specified magnitude. The filtered signal is transmitted to a logic and timing circuit connected to the output of the threshold discriminating mechanism which counts pulses received from the threshold detecting mechanism in a specified period of time and produces an output signal depending upon the count rate.

DETAILED DESCRIPTION OF PREFERRED EMBODIMENTS

15 In one embodiment of the present invention, hydrogen and hydrogen-containing compounds in gas or thin film samples are detected by detecting the presence of recoil protons which pass through a degrading foil such as aluminum, silicon, gold, copper, or magnesium, after collisions between hydrogen nuclei and alpha particles from an alpha particle source, such as $^{241}$Am, $^{230}$U, $^{223}$Ra, $^{228}$Th, $^{232}$U, $^{208}$Po, $^{229}$Th, $^{227}$Ac, $^{209}$Po, and $^{226}$Ra. As used herein, "degrading foil" refers to any substance which is ionized through the loss of kinetic energy as a charged particle travels through the substance.

Figure 1:
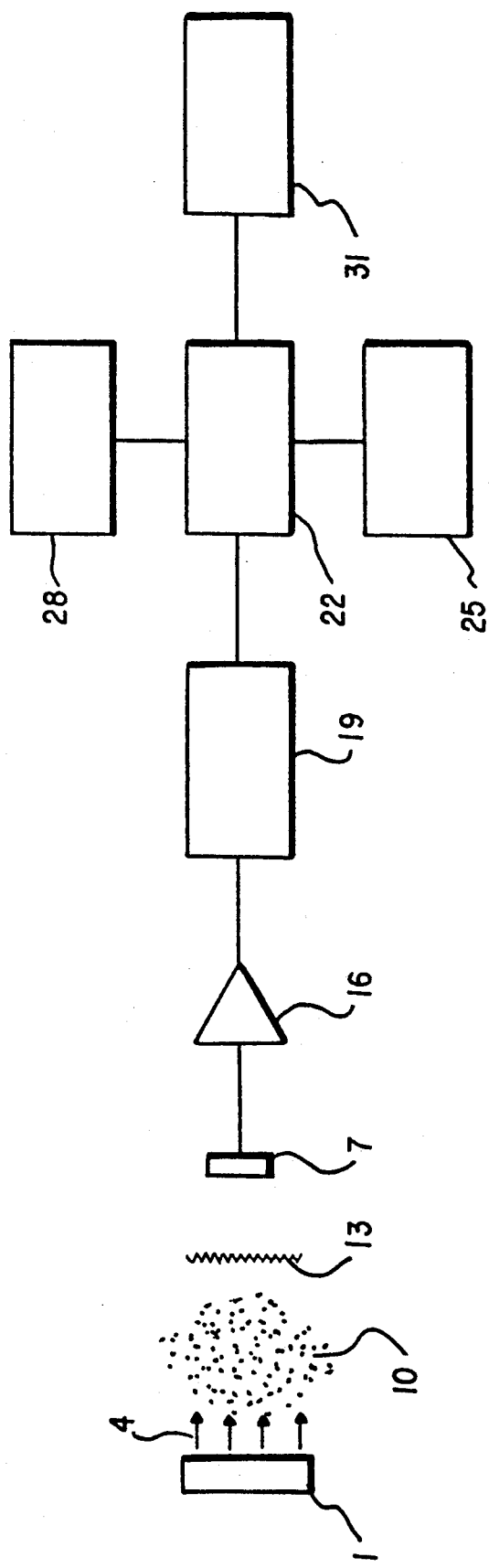
FIG. 1 is a schematic view of an embodiment of the hydrogen detecting apparatus of the instant invention.

Referring to FIG. 1, an alpha particle source 1 producing alpha particles 4 with energies ranging from 4 to 8 MeV is placed within a distance of about 1 to 5 cm of a detector 7. The distance is based on the anticipated energy loss of the alpha particle in air. Detector 7 may be any device capable of detecting recoil protons. Other potential detectors include a scintillation detector, a spark chamber, and a proportional counter, but a solid state diode is preferred. Potential alpha particle sources are any radioactive nuclide which produce alpha particles with kinetic energies above about 4 MeV, including $^{241}$Am, $^{230}$U, $^{223}$Ra, $^{228}$Th, $^{232}$U, $^{208}$Po, $^{229}$Th, $^{227}$Ac, $^{209}$Po, and $^{226}$Ra.

Alpha particles 4 released from the alpha particle source 1 collide with hydrogen nuclei present in a sample medium 10 located between the alpha particle source 1 and the detector 7. Although FIG. 1 depicts the sample medium 10 as a gas, the measurement of hydrogen in thin solid samples (e.g. thin films) is also possible with the subject invention so long as the thickness of the film permits passage of the recoil protons.

Collisions between the alpha particles 4 and the hydrogen nuclei, if any, present in the sample medium 10 produce recoil protons with kinetic energy of about one half of the kinetic energy of the incident alpha particles. Collisions between the alpha particles 4 and nuclei of atoms other than hydrogen produce neither recoil protons nor neutrons for the reason that the binding energies of the protons and neutrons in the nuclei are greater than the kinetic energies of the alpha particles 4.

The recoil protons and alpha particles 4 with the proper trajectories strike a degrading foil 13 which stops substantially all of the alpha particles and other noise-producing media such as light but passes substantially all of the recoil protons. While not wishing to be bound by any theory, it appears that the energy degrading foil 13 substantially blocks all particles other than recoil protons for the reasons that most other particles are heavier and have greater charge than recoil protons and are less likely to pass through a degrading foil of a given thickness than recoil protons. The degrading foil 13 may be located anywhere between the sample medium 10 and detector 7. The degrading foil 13 may also be located on the face of the detector 7 where it will protect the sensitive detector face from dust and other contaminants. If a metal degrading foil is employed, the degrading foil 13 may be electroplated or sputtered on the face of the detector 7.

The selection of the composition and thickness of the degrading foil 13 is primarily based upon the Mean Ion Depth and the Longitudinal Straggling. The Mean Ion Depth of a degrading foil is the mean value of the final depth distribution of particles having specific ion energies, which have penetrated the degrading foil. The Mean Ion Depth will depend upon a number of factors including particle identity, initial particle energy, composition of the degrading foil and the nature and frequency of collisions between atoms in the degrading foil and the particle.

Longitudinal Straggling of a degrading foil is the square-root of the second moment (or standard deviation) of the final depth distribution of particles having specific ion energies, which have penetrated the degrading foil. Longitudinal Straggling, like Mean Ion Depth, is a function of particle identity, particle energy, composition of the degrading foil, and the nature and frequency of collisions between atoms in the degrading foil and the particle. U. Kittmark & J. F. Ziegler, "*Handbook of Range Distributions for Energetic Ions In All Elements*," vol. 6 (1980) presents tables showing the Mean Ion Depth and Longitudinal Straggling for different degrading foils as a function of the ion energy of various types of particles penetrating the degrading foil.

The degrading foil 13 should be of an appropriate composition and thickness such that alpha particles are substantially prevented from penetrating the degrading foil 13 and recoil protons are substantially capable of passing through the degrading foil 13. For example, the composition and thickness of the degrading foil are selected such that the Mean Ion Depth for recoil protons is greater than the sum of the Mean Ion Depth for alpha particles plus about three times the Longitudinal Straggling for such alpha particles (for threshold hydrogen detection), based on the assumption that one million alpha particles must be blocked for each recoil proton. The preferred thickness is greater than the sum of the Mean Ion Depth for alpha particles plus about four times the Longitudinal Straggling for such particles based on the assumption that ten million alpha particles must be blocked for each recoil proton. Other desired characteristics of possible degrading foils 13 are low cost, the capability of the degrading foil to be applied in micron scale depths at a uniform thickness, and the stability of the degrading foil over time. The preferred degrading foil 13 is aluminum having a thickness of approximately 15 to 20 microns, preferably around 17 microns. Among other preferred materials are metals such as gold, copper, and magnesium, and nonmetals such as silicon dioxide (glass).

With such degrading foils, substantially all recoil protons, but substantially no alpha particles, will pass through the degrading foil 13. This is so because recoil protons have a significantly greater penetration depth in matter than alpha particles of comparable energy. In this manner, the false signals generated by the impact of alpha particles on the detector 7 will be substantially reduced.

Detector 7 detects the number of recoil protons passing through the energy degrading foil 13. Detector 7 is preferably a silicon or germanium-based semiconductor which is capable of being doped to produce both n-type and p-type regions and has a depletion layer ranging from about 5 to 40 microns in thickness, preferably about 20 microns based on the Mean Ion Depth and Longitudinal Straggling for 1 MeV recoil protons. When charged particles, such as recoil protons and alpha particles, contact the detector 7, they dislodge a number of electrons in the depletion layer proportional to their kinetic energies. The dislodged electrons and electron holes are transported by the electric field created by the n-type and p-type regions of the detector 7, thereby generating an electrical current. The thickness of the depletion layer should be such that the recoil protons deposit a substantial fraction of their energy in the depletion layer and such that this energy results in a signal that is above the background noise in the detecting circuitry.

The recoil protons and those undesired alpha particles which penetrate the energy-degrading foil 13 impact the detector 7 and produce an electrical signal which is amplified in amplifier 16. Amplifier 16 may be any electrical amplifying device, preferably of about 10 dB to 40 dB gain, preferably 30 dB gain. The amplified signal is preferably passed through a threshold discriminator 19 which eliminates undesirable low-energy signals arising from x-rays, gamma-rays, and beta particles produced by the alpha source, and other types of low energy electrical noise. The threshold discriminator 19 is any device capable of filtering electrical signals of different magnitudes and is preferably designed to disregard electrical signals below a threshold less than about 0.1 to 0.2 MeV based on a 5 MeV alpha particle source. The proper threshold will, of course, depend upon the alpha particle source, the degrading foil characteristics, and the amount of noise produced by other sources.

The accuracy of the threshold discriminator 19 may be further increased by the use of a Poisson distribution to eliminate undesired signals. A Poisson distribution describing the expected time between successive counts for a given concentration of hydrogen is used to determine a minimum acceptable time interval between counts. Two counts which occur within this minimum time interval are deemed to be due to noise rather than recoil protons, and are therefore ignored. One method for accomplishing this is to turn off the counting circuit for this minimum time interval after each count thus eliminating the possibility of counting a second signal within the minimum time interval. The minimum acceptable time interval between counts is the time interval in the Poisson distribution at which there is a probability of from about 0.1% to 10% that two counts from recoil protons will fall within the time interval. The preferred probability is a probability of about 1%.

The output of the threshold discriminator 19 is preferably supplied to a logic circuit 22 which counts the electrical signals to measure the concentration of hydrogen in the sample medium 10. The logic circuit 22 may be any device capable of counting discrete electrical signals as a function of time. A timing circuit 25 passes elapsed time information to the logic circuit 22 which determines the number of electrical signals in a specified time period (e.g., count). The timing circuit 25 may be any device which records elapsed time.

The output of the logic circuit 22 depends on the count. If the count is below the unsafe level, a safe signal is passed to the alarm/display circuit 31. If the count is above the unsafe level, a danger signal is passed to the alarm/display circuit 31.

The unsafe level is defined as a fraction (roughly two thirds) of the lower explosive limit of the anticipated combustible gases. For example, the lower explosive limit for methane is 5.3% by volume in air and for propane is 2.3% by volume which is equivalent in hydrogen content to a methane concentration of 4.6% by volume. The lower explosive limit for hydrogen gas is 4.1% by volume which is equivalent in hydrogen content to a methane concentration of 2% by volume. N. Sax, *Dangerous Properties of Industrial Materials*, (5th Ed. 1979).

Because water vapor contains hydrogen, an adjustment is necessary to prevent the logic circuit 31 from triggering an alarm as a result of high humidity. One method is to define the unsafe level such that the hydrogen concentration from water molecules will not trigger the alarm. For example, a relative humidity of 100% at 80° F. will be measured by the logic circuit 22 as equivalent to approximately 2% concentration of methane. Accordingly, the unsafe level may be defined high enough so that the relative humidities typically encountered in the desired location are not sufficient to trigger the alarm.

Alternatively, a humidity correction apparatus 28 may be employed to adjust the unsafe level based upon the relative humidity in the ambient atmosphere when the measurement is made by the logic circuit 22. The humidity correction apparatus 28 may be any device capable of measuring and compensating for the humidity level. In one approach, the humidity correction apparatus 28 comprises a capacitor in which the space between the capacitor plates contains a porous insulator. The porous insulator will absorb humidity and consequently experience a change in dielectric behavior due to the presence of water. It is important that the porous insulator absorb but not retain water molecules for a significant length of time. Otherwise, the humidity correction apparatus will register too high a level of humidity.

The humidity correction apparatus 28 provides an electrical signal proportional to the relative humidity in the sample medium 10 to the logic circuit 22, which increases the unsafe level proportional to the magnitude of the electrical signal. Data used to calibrate the logic circuit 22 is obtained by operating the humidity correction apparatus 28 in a controlled humidity environment at different levels of humidity ranging from 0% up to 100% and from 100% humidity down to 0%. It is desirable that the porous capacitor reproduce the original capacitance at 0% humidity when humidity level is returned to 0%. The porous insulator may be any number of hydrophilic substances, including air and polypropylene. As will be appreciated by those skilled in the art, the humidity correction apparatus 28 may also be any other humidity sensor that produces a usable signal or output.

Although the present invention is capable of neither distinguishing nor selectively measuring specific hydrogen-containing compounds when other hydrogen-containing compounds are present, the concentration of the harmless hydrogen-containing compound typically found in ambient air, water vapor, is selectively measured by the humidity correction apparatus 28. In the unlikely event that a number of other hydrogen-containing compounds are in the sample medium 10, they will most likely be either explosive or toxic. Accordingly, the triggering of the alarm/display circuit 31 due to a hydrogen concentration in excess of the unsafe level, though not necessarily attributable to a specific hydrogen-containing compound, is nonetheless effective in detecting many unsafe conditions.

Figure 2:
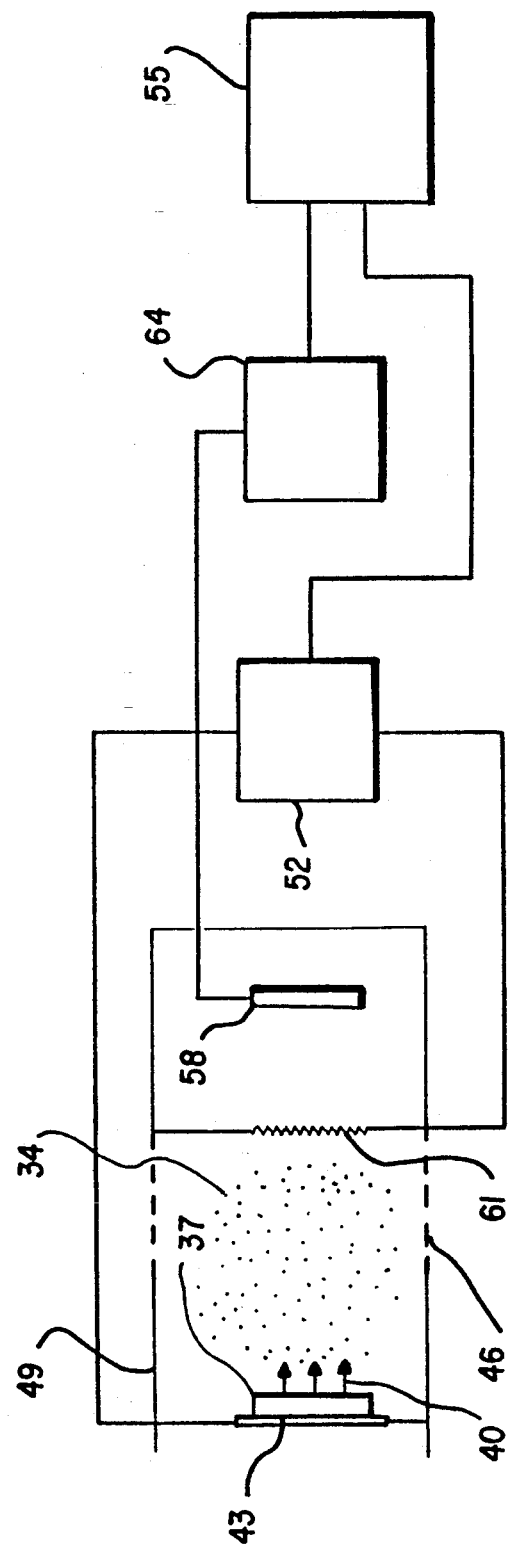
FIG. 2 is a schematic view of a combined hydrogen and smoke detector using the same alpha particle source.

Referring to FIG. 2, another embodiment of the present invention, a low-cost combination gas and smoke detector is illustrated. Since alpha sources are commonly used in smoke detectors as well as the present invention, it is possible to use the same alpha source 37 both to ionize the medium for detection of smoke and produce recoil protons if hydrogen is present in the sample medium 34. The alpha source 37 may be located anywhere in the sample medium 34, preferably adjacent to the ionization electrode 43 or wall of the detection chamber 49.

With respect to the smoke detecting assembly, which consists of ionization electrode 43, degrading foil 61, amplifying and comparing circuitry 52, and alarm 55, a low electric current caused by ionization of air by alpha particles 40 will flow through the air between the ionization detection electrode 43 and the degrading foil 61, which acts as an electrode. The degrading foil 61 is composed of any electrically conductive material and is connected to the ionization detection electrode 43 to enable the degrading foil 61 to act as a second ionization detection electrode. As will be appreciated by one skilled in the art, it is possible to use a second ionization electrode other than the degrading foil 61 but such configurations are not preferred.

Ambient air enters through openings 46 in the detection chamber 49. Smoke particles in the air in detection chamber 49 increase electrical resistance so that less current flows between the ionization electrode 43 and the degrading foil 61. The current is preferably monitored by amplifying and comparing circuitry 64 which is the amplifying and comparing circuitry normally used in smoke detectors. The amplifying and comparing circuitry 64 responds to a reduction in current caused by smoke by triggering the alarm 55.

With respect to the hydrogen detecting assembly, which consists of degrading foil 61, detector 58, amplifying and comparing circuitry 64, and alarm 55, alpha particles 40 and recoil protons contact degrading foil 61. As described above, degrading foil 61 blocks substantially all alpha particles 40 from contacting the detector 58 but permits substantially all recoil protons to contact the detector 58. Amplifying and comparing circuitry 64 includes an amplifier, threshold discriminator, logic and timing circuits, and humidity correction apparatus, which operate in the same manner as described earlier. Alarm 55 is connected to the output of both amplifying and comparing circuitry 52 and 64 to signal the presence of either hydrogen or hydrogen-containing compounds or smoke.

Figure 3:
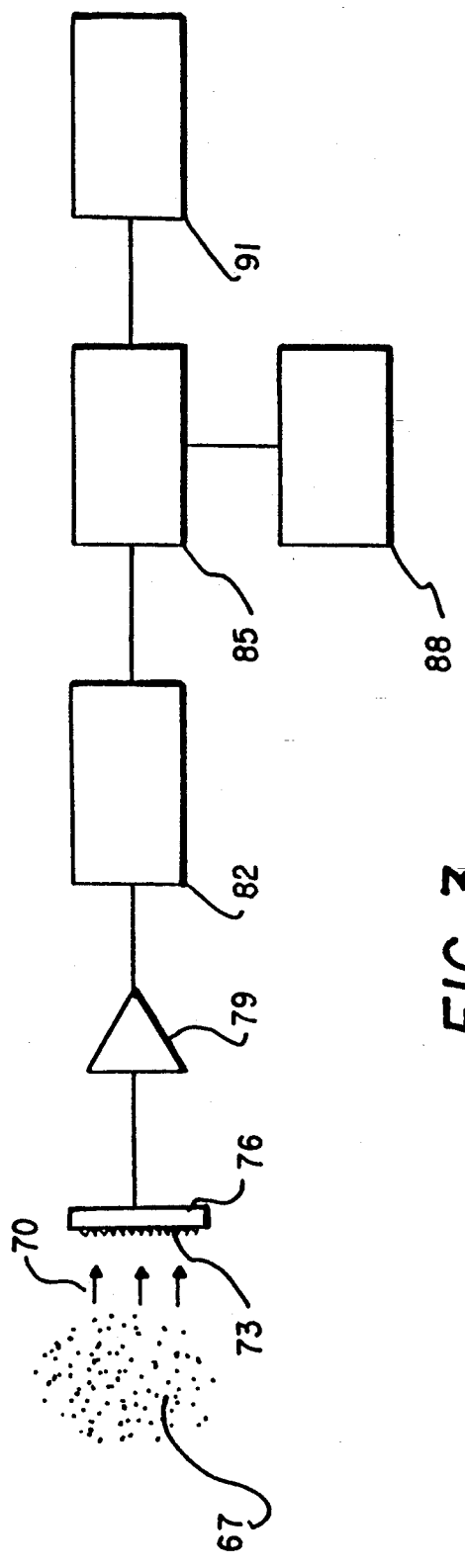
FIG. 3 is a schematic view of radon detector apparatus including an energy degrading foil.

Referring to FIG. 3, another embodiment of the present invention, a solid-state diode-type radon detector is illustrated. Decaying radon and radon daughters in sample medium 67 are the source of alpha particles 70. The alpha particles 70 contact the degrading foil 73, located either between the detector 76 and sample medium 67 or on the detector face. Detector 76 has the degrading foil 73 mounted on the face of the detector 76.

The degrading foil 73 may be any degrading foil that is of a sufficient thickness to substantially block light and other undesirable particles but substantially pass alpha particles. Alpha particles typically have kinetic energies ranging from 5 to 8 MeV. Based on Maissel and Glang, *Handbook of Thin Film Technology*, (1970), the degrading foil thickness necessary for blocking light is 0.1 to 0.2 microns for an aluminum foil. The thickness will, of course, vary based on the composition of the degrading foil but the thickness will typically be in the tenths of microns.

Detector 76 includes a depletion layer located close enough to the degrading foil 73 to permit alpha particles 70 passing through the degrading foil 73 to deposit their energy in the depletion layer. Detector 76 is preferably a silicon or germanium-based compound capable of being doped to produce both n-type and p-type regions. For alpha particles with energies ranging from about 5 to 8 MeV, the depletion layer should have a thickness preferably between about 5 to 10 microns. As will be known and understood by one skilled in the art, other potential alpha particle detectors producing a usable signal may be used including track etch dosimeters, thermoluminescent dosimeters, surface barrier dosimeters, scintillation detectors, ionization detectors and proportional counters.

Another type of radioactive particle released by a radioactive source, beta particles, may be measured by the present invention along with alpha particles by increasing the thickness of the depletion layer to about 300 to 500 microns. If the thickness is not increased, neither beta particles nor gamma particles, another type of radioactive particle released by a radioactive source, will be accurately measured by the present invention but will generate low magnitude noise due to the deposition of a small portion of their kinetic energy in the depletion layer. In light of the dramatically greater penetrability of beta and gamma particles compared to alpha particles, the present invention detects radioactive sources based on the measurement of alpha particles and not beta or gamma particles.

Detector 76 produces an electrical pulse which is amplified by amplifier 79 and passed through a threshold discriminator 82 preferably to a logic circuit 85. As in the first embodiment, the threshold discriminator 82 has a threshold sufficient to eliminate substantially all electrical pulses produced by undesired substances striking the detector 76 as well as other forms of noise. In most applications, the threshold will be about 0.5 MeV. Additionally, a Poisson distribution may be used to further increase the accuracy of the threshold discriminator 82 as discussed earlier.

Logic circuit 85 is preferably connected to a timing circuit 88 which passes elapsed time information to the logic circuit 85 to determine the number of electrical pulses in a specified time period. The output of logic circuit 85 is preferably passed to display 91 where radon levels are indicated.

In light of the proceeding discussion of the above embodiments, a number of advantages of the present invention are apparent. First, the present invention provides a compact and inexpensive device to detect hydrogen-containing compounds or radon and radon daughters in a desired sample and is suitable for residential and industrial applications. The detecting apparatus and supporting circuitry for all three embodiments is compact enough to fit within the casing of existing smoke detectors designed for household use. Each embodiment also may be powered by a standard 9 volt battery. Second, the present invention is capable of detecting hydrogen-containing compounds other than water in a sample. This benefit provides greater accuracy in the detection of explosive and/or toxic concentrations of hydrogen-containing compounds. Third, the characteristics of the degrading foil may be optimized such that a maximum number of recoil protons and minimum number of alpha particles contact the charged particle detector. In this manner, a more accurate measurement of hydrogen-containing compounds is possible than in existing devices. Fourth, the present invention provides an accurate and instantaneous concentration of hydrogen or radon and radon daughters in a sample at any point in time. Finally, the present invention combines the advantages of a smoke and hydrogen detector into a single, simple, and inexpensive device suitable for use in residential and industrial applications. Such a device provides a greater level of safety for consumers than existing smoke detectors, which are used only for smoke detector and hydrogen-detecting devices which are used to detect only hydrogen.

As will be appreciated by one skilled in the art, the purpose of the present invention can be accomplished by using suitable devices other than the specific devices described above. For example, recoil protons may be measured by detectors other than charged particle detectors.

The following example is provided for illustration and is not intended to limit the scope of the invention.

EXAMPLE

Figure 4:
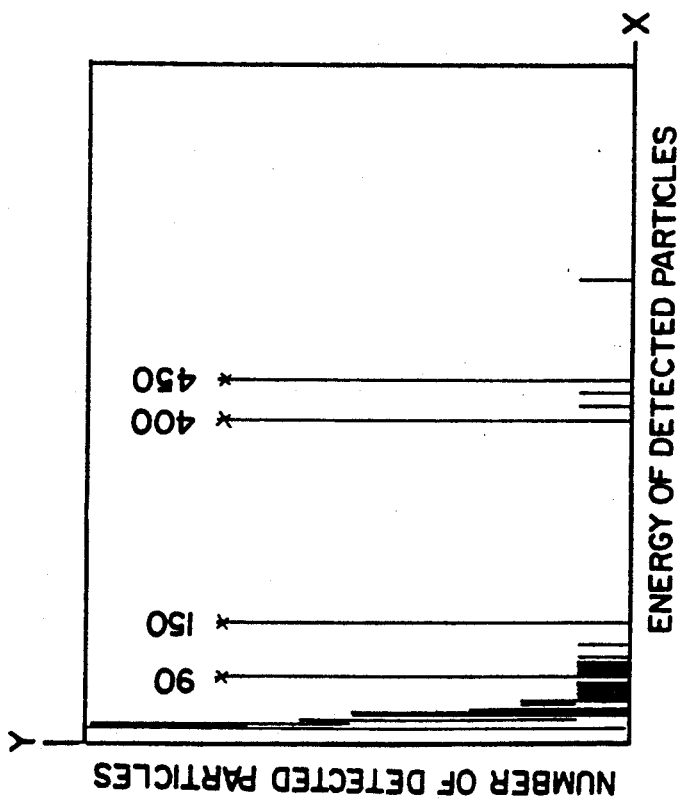
FIG. 4 illustrates the charged particle spectrum produced by a 5.5 MeV $^{241}$Am alpha particle source through an energy degrading foil with no hydrogen present.

FIG. 4 is a tracing from a calibrated 1024 multi-channel analyzer showing the charged particle spectrum produced by a 5.5 MeV $^{241}$Am alpha particle source through an energy-degrading foil with no hydrogen present. The spectrum is based on a two-minute run under ambient atmospheric conditions and represents the background calibration for the system.

Figure 5:
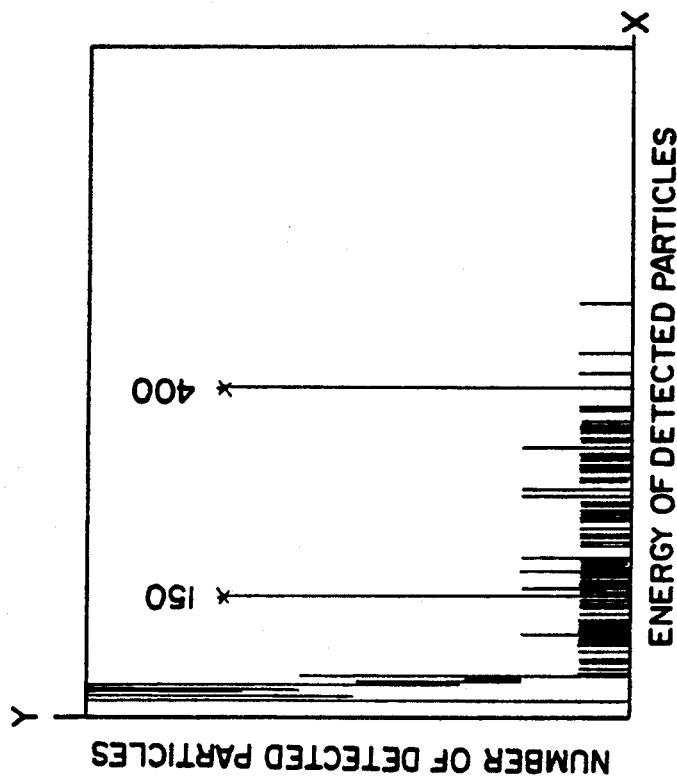
FIG. 5 illustrates the charged particle spectrum produced by a 5.5 MeV $^{241}$Am alpha particle source through a hydrogen-containing material (Mylar ™).

FIG. 5 illustrates the output and operation of the threshold discriminator 19. FIG. 5 is also a tracing from the same calibrated 1024 multi-channel analyzer showing the charged particle spectrum produced by a 5.5 MeV $^{241}$Am alpha particle source through an energy-degrading foil with a hydrogen-containing material (Mylar TM) present. The thickness of the Mylar TM was chosen to simulate a methane concentration of about 10% by volume. The spectrum is based on a two-minute run under ambient atmospheric conditions.

As shown in FIG. 4, when a threshold equivalent to a channel of 150, which equates to 0.4 MeV in this test, is selected for the threshold discriminator 22, the majority of background noise is eliminated from the detecting apparatus. FIG. 5 illustrates that with the threshold set at a channel of 150 the detecting apparatus provides an accurate determination of the hydrogen content of the sample medium. Using the present invention, the measured hydrogen concentration for the Mylar TM was equivalent to 10.2% by volume of methane, which is only about 2% different from the actual concentration.

While various embodiments of the present invention have been described in detail, it is apparent that modifications and adaptations of those embodiments will occur to those skilled in the art. However, it is to be expressly understood that such modifications and adaptations are within the scope of the present invention, as set forth in the following claims.

What is claimed is:

1. An apparatus for detecting hydrogen, comprising:
    a) a source of alpha particles positioned to cause alpha particles to contact a sample;
    b) an energy degrading medium; and
    c) detecting means positioned on the side of said energy degrading medium opposite said source of alpha particles;
    wherein:
        (1) the thickness of said energy degrading medium is greater than the sum of the Mean Ion Depth in said energy degrading medium for said alpha particles plus three times the Longitudinal Straggling in said energy degrading medium for said alpha particles; and
        (2) the composition of the energy degrading medium is selected such that the Mean Ion Depth in said energy degrading medium for recoil protons produced when said alpha particles contact hydrogen nuclei in said sample is greater than said thickness.

2. An apparatus, as claimed in claim 1, wherein said energy degrading medium is a degrading foil.

3. An apparatus, as claimed in claim 2, wherein said degrading foil is a metal foil.

4. An apparatus, as claimed in claim 1, further comprising amplifying means connected to said detecting means to amplify the signal produced by said detecting means.

5. An apparatus, as claimed in claim 4, further comprising threshold discriminating means connected to said amplifying means to eliminate substantially all signals received from said amplifying means below a specified magnitude.

6. An apparatus, as claimed in claim 5, further comprising logic and timing means connected to the output of said threshold discriminating means to count pulses received from said threshold discriminating means in a specified period of time and produce a signal based upon the count.

7. An apparatus, as claimed in claim 1, further comprising humidity measuring means to produce a signal proportional to the concentration of $H_2O$ in said sample.

8. An apparatus, as claimed in claim 1, further comprising ionization-level detecting means for detecting smoke, said ionization-level detecting means including a detection chamber for receiving ambient air wherein said ionization-level detecting means utilizes said source to ionize said air in said detection chamber.

9. An apparatus, as claimed in claim 8, wherein said ionization level detecting means further comprises at least two electrodes and said energy degrading foil comprises one of said electrodes.

10. An apparatus, as claimed in claim 1, wherein said detecting means has a surface facing said sample and said degrading medium is located on said surface.

11. An apparatus, as claimed in claim 1, wherein said detecting means includes a depletion layer located a predetermined distance from said energy degrading medium sufficient for said recoil protons passing through said energy degrading medium to deposit energy in said depletion layer.

12. An apparatus, as claimed in claim 11, wherein said detecting means produces a signal proportional to the energy produced in said depletion layer by recoil protons produced when said alpha particles contact hydrogen nuclei in said sample.

13. An apparatus, as claimed in claim 1, wherein said energy degrading medium is located in line of sight of said source.

14. An apparatus, as claimed in claim 1, wherein said thickness of said energy degrading medium is sufficient to block at least one million of said alpha particles for each of said recoil protons contacting said detecting means.

15. An apparatus, as claimed in claim 1, wherein said thickness of said energy degrading medium is greater than the sum of the Mean Ion Depth in said energy degrading medium for said alpha particles plus four times the Longitudinal Straggling in said energy degrading medium for said alpha particles.

16. An apparatus, as claimed in claim 1, wherein said thickness of said energy degrading medium is sufficient to block at least ten million of said alpha particles for each of said recoil protons contacting said detecting means.

17. An apparatus, as claimed in claim 1, wherein said energy degrading medium comprises aluminum and said energy degrading medium thickness is approximately 15 to 20 microns.

18. A method of detecting hydrogen comprising the steps of:
  a) directing alpha particles into a sample;
  b) blocking said alpha particles with an energy degrading medium having:
    (1) a thickness greater than the sum of the Mean Ion Depth in said energy degrading medium for said alpha particles plus three times the Longitudinal Straggling in said energy degrading medium for said alpha particles; and
    (2) a composition such that the Mean Ion Depth in said energy degrading medium for recoil protons produced when said alpha particles contact hydrogen nuclei in said sample is greater than said thickness; and
  c) detecting the quantity of said recoil protons which pass through said energy degrading medium.

19. A method, as claimed in claim 18, further comprising the steps of:
  amplifying a signal from the detector;
  eliminating signals from the amplifier below a specified magnitude;
  counting signals above said specified magnitude; and
  producing an output based on the count.

20. A method, as claimed in claim 18, wherein said alpha particles are capable of proceeding directly through said sample toward the detector in a straight line manner.

21. An apparatus for detecting hydrogen, comprising:
  (a) a source of alpha particles positioned to cause alpha particles to contact a sample to produce recoil protons when said alpha particles contact hydrogen nuclei in said sample;
  (b) an energy degrading medium; and
  (c) detecting means positioned on the side of said energy degrading medium opposite said source of alpha particles, wherein the thickness and composition of said energy degrading medium is selected such that for each of said recoil protons contacting said detecting means, said degrading medium blocks at least one million alpha particles.

22. An apparatus, as claimed in claim 21, wherein said energy degrading medium is located in line of sight of said source.

23. An apparatus, as claimed in claim 21, wherein said thickness of said energy degrading medium is greater than the sum of the Mean Ion Depth in said energy degrading medium for said alpha particles plus three times the Longitudinal Straggling in said degrading medium for said alpha particles.

24. An apparatus, as claimed in claim 21, wherein said thickness of said energy degrading medium is greater than the sum of the Mean Ion Depth in said energy degrading medium for said alpha particles plus four times the Longitudinal Straggling in said energy degrading medium for said alpha particles.

25. An apparatus, as claimed in claim 21, wherein said energy degrading medium comprises aluminum and said energy degrading medium thickness is approximately 15 to 20 microns.

26. An apparatus, as claimed in claim 21, further comprising humidity measuring means to produce a signal proportional to the concentration of $H_2O$ in said sample.

* * * * *